(12) United States Patent
Canfield et al.

(10) Patent No.: US 11,896,434 B2
(45) Date of Patent: Feb. 13, 2024

(54) SYSTEMS AND METHODS FOR FRAME INDEXING AND IMAGE REVIEW

(71) Applicant: KONINKLIJKE PHILIPS N.V., Eindhoven (NL)

(72) Inventors: Earl M. Canfield, New Braunfels, TX (US); Thanasis Loupas, Kirkland, WA (US); Robert Gustav Trahms, Edmonds, WA (US); David Hope Simpson, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 300 days.

(21) Appl. No.: 17/299,851

(22) PCT Filed: Dec. 11, 2019

(86) PCT No.: PCT/EP2019/084534
§ 371 (c)(1),
(2) Date: Jun. 4, 2021

(87) PCT Pub. No.: WO2020/126712
PCT Pub. Date: Jun. 25, 2020

(65) Prior Publication Data
US 2022/0071600 A1   Mar. 10, 2022

Related U.S. Application Data

(60) Provisional application No. 62/780,354, filed on Dec. 17, 2018.

(51) Int. Cl.
*A61B 8/08* (2006.01)
*A61B 8/00* (2006.01)
*G06N 3/08* (2023.01)

(52) U.S. Cl.
CPC .......... *A61B 8/5223* (2013.01); *A61B 8/0866* (2013.01); *A61B 8/469* (2013.01); *G06N 3/08* (2013.01)

(58) Field of Classification Search
CPC ..... A61B 8/5223; A61B 8/0866; A61B 8/469; A61B 8/085; A61B 8/463; A61B 8/0883;
(Continued)

(56) References Cited

U.S. PATENT DOCUMENTS 6,126,599 A * 10/2000 Jago .................... G01S 7/52025
600/443
6,213,945 B1 * 4/2001 Tynan .................... A61B 8/461
600/441
(Continued)

FOREIGN PATENT DOCUMENTS

WO   2018009405 A1   1/2018
WO   2018060723 A1   4/2018
(Continued)

OTHER PUBLICATIONS

Bakas et al:"Spot The Best Frame: Towards Intelligent Automated Selection of the Optimal Frame for Initialisation of Focal Liver Lesion Candidates in Contrast-Enhanced Ltrasound Video Sequences"; IEEE 2013 9th Confernece on Intelligent Environments, pp. 96-203.
(Continued)

*Primary Examiner* — Sanjay Cattungal

(57) ABSTRACT

The present disclosure describes imaging systems configured to generate index information to indicate which image frames in a plurality of image frames include one or more target anatomical features, such as a head or femur of a fetus. The confidence levels of the presence of the target anatomical features are also determined. The system may be configured to determine if the target anatomical feature is present in an image frame by implementing at least one neural network. Merit levels based on the quality of the
(Continued)

image frames may also be determined. Measurements of the one or more items of interest may be acquired. Visual representations (500) of the index information (502), confidence levels, merit levels, and/or measurements may be provided via a user interface. A user interface may receive user inputs based on the visual representations to navigate to specific image frames (508) of the plurality of image frames.

15 Claims, 13 Drawing Sheets

(58) Field of Classification Search
CPC .......... G06N 3/08; G06N 3/044; G06N 3/045; G06N 3/088
See application file for complete search history.

(56) References Cited

U.S. PATENT DOCUMENTS

| | | | | |
|---|---|---|---|---|
| 6,524,246 B1* | 2/2003 | Kelly | ............... | B82Y 15/00 600/437 |
| 7,645,238 B2* | 1/2010 | Hirsh | ............... | A61B 8/4461 600/463 |
| 7,931,594 B2* | 4/2011 | Hirsh | ............... | A61B 8/42 600/463 |
| 9,177,110 B1* | 11/2015 | Fram | ............... | G06T 11/60 |
| 9,852,272 B1* | 12/2017 | Fram | ............... | G16H 10/40 |
| 2004/0225221 A1* | 11/2004 | Olsson | ............... | A61B 8/5238 600/447 |
| 2004/0267122 A1* | 12/2004 | Nadadur | ............... | A61B 8/467 600/440 |
| 2007/0016029 A1* | 1/2007 | Donaldson | ............... | A61B 8/565 600/437 |
| 2009/0299182 A1* | 12/2009 | Asafusa | ............... | A61B 8/481 600/458 |
| 2011/0311116 A1* | 12/2011 | Benn | ............... | G06T 11/00 382/128 |
| 2012/0078097 A1* | 3/2012 | Wang | ............... | A61B 8/0883 600/437 |
| 2013/0190600 A1* | 7/2013 | Gupta | ............... | A61B 8/0866 600/407 |
| 2013/0345563 A1* | 12/2013 | Stuebe | ............... | A61B 5/316 600/440 |
| 2016/0081663 A1* | 3/2016 | Chen | ............... | G06T 7/62 600/407 |
| 2016/0110632 A1* | 4/2016 | Kiraly | ............... | G06T 7/11 382/128 |
| 2016/0173770 A1* | 6/2016 | Fosodeder | ............... | A61B 8/5207 348/77 |
| 2016/0331345 A1* | 11/2016 | Kong | ............... | A61B 8/5207 |
| 2016/0345936 A1* | 12/2016 | Cho | ............... | G01S 7/52084 |
| 2017/0024883 A1 | 1/2017 | Urabe et al. | | |
| 2017/0124701 A1* | 5/2017 | Liang | ............... | G06T 7/11 |
| 2017/0148190 A1* | 5/2017 | Kim | ............... | A61B 8/5292 |
| 2018/0103912 A1 | 12/2018 | Canfield et al. | | |

FOREIGN PATENT DOCUMENTS

| | | |
|---|---|---|
| WO | 2019201726 A1 | 10/2019 |
| WO | 2020038781 A1 | 2/2020 |

OTHER PUBLICATIONS

Baumgartner et al.: "Sononet: Real-Time Detection and Localisation of Fetal Standard Scan Planes in Freehand Ultrasound"; IEEE Transactions on Medical Imaging, vol. 36, No. 11, Nov. 2017, pp. 2204-2215.

De Vos et al.: "Convnet-Based Localization of Anatomical Structures in 3D Medical Images"; IEEE Transactions on Medical Imaging, 2017, 12 Page Document.

PCT/EP2019/084534 ISR & WO, Apr. 8, 2020, 18 Page Document.

* cited by examiner

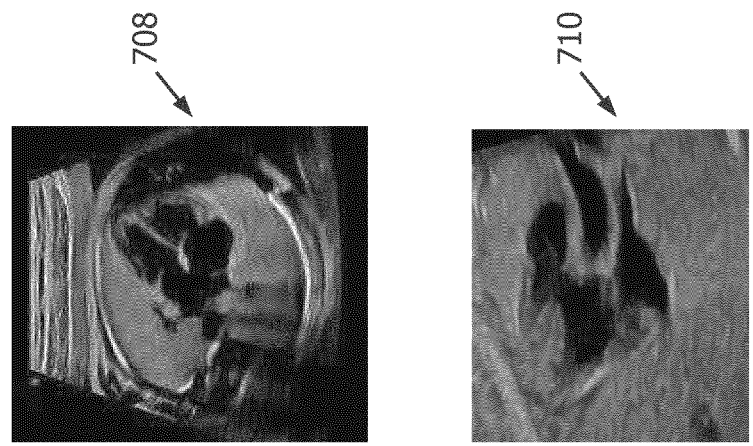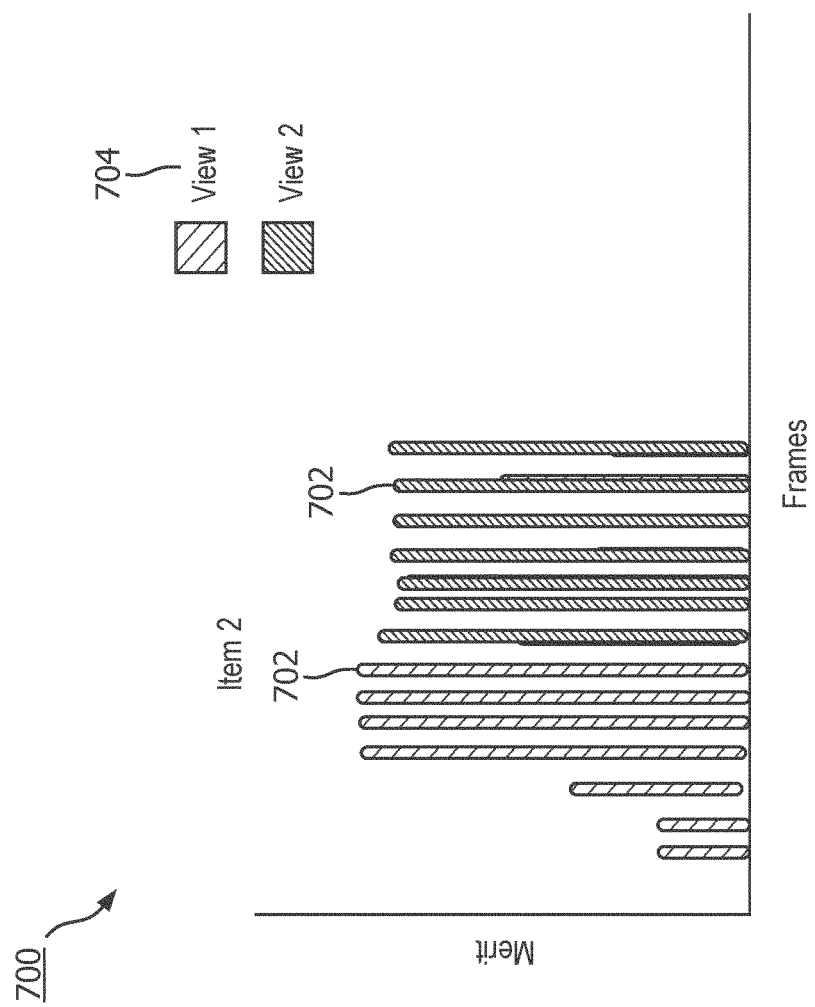
FIG. 7

SYSTEMS AND METHODS FOR FRAME INDEXING AND IMAGE REVIEW

CROSS-REFERENCE TO PRIOR APPLICATIONS

This application is the U.S. National Phase application under 35 U.S.C. §371 of International Application No. PCT/EP2019/084534, filed on Dec. 11, 2019, which claims the benefit of U.S. Provisional Patent Application No. 62/780,354, filed on Dec. 17, 2018. These applications are hereby incorporated by reference herein.

TECHNICAL FIELD

The present disclosure pertains to imaging systems and methods for determining which acquired image frames include an item of interest and providing a visual representation of the determination using at least one neural network. Particular implementations involve systems configured to generate displays indicating the items of interest in each image frame obtained via an ultrasound imaging system.

BACKGROUND

During an imaging exam, such as an ultrasound exam, numerous images may be acquired as still image frames or as sequences of image frames often referred to as cineloops. Hundreds or thousands of image frames, either still frames or cineloops, may be acquired and stored for later review. When reviewing a previous exam, a user, such as a radiologist, must individually review each recorded image frame to find acceptable images of anatomy or pathology for performing measurements and/or diagnostic assessments. A user, such as a sonographer, may have to review recorded image frames during an exam to confirm that acceptable images of anatomy or pathology have been acquired. In either setting, this manual review of numerous image frames is time consuming. In the example described with the radiologist, the lengthy review limits the number of patient files that can be processed. In the example described with the sonographer, not only does the cumbersome review process limit the number of patients that can be scanned by the sonographer, the length of each exam is increased, which inconveniences the patient. Accordingly, new technologies to reduce the time required to review image frames are needed.

SUMMARY

The present disclosure describes systems and methods for reviewing acquired ultrasound image frames. More specifically, the systems and methods may be configured to determine which image frames include one or more items of interest and generate index information based on the determination. A visual representation of the index information may be displayed on a user interface. This visual representation may allow a user to find which image frames to review to make a desired measurement and/or diagnosis. In some embodiments, the system may make one or more measurements automatically.

In accordance with some embodiments described herein, an ultrasound imaging system may include an ultrasound transducer configured to acquire echo signals responsive to ultrasound pulses transmitted toward a region of interest, one or more processors in communication with the ultrasound transducer and configured to: receive a plurality of image frames generated from the ultrasound echoes, determine, for each image frame of the plurality of image frames, whether target anatomical feature is present in the image frames, and generate, for each of the image frames of the plurality of image frames, index information based on a confidence level indicating the target anatomical feature is present in the given image frame. The ultrasound imaging system may include a user interface in communication with the one or more processors and configured to display a visual representation of the index information.

In accordance with some embodiments described herein, acquiring echo signals responsive to ultrasound pulses transmitted into a region of interest by a transducer operatively coupled to an ultrasound system, generating a plurality of image frames from the ultrasound echoes, processing each of a plurality of image frames to determine a confidence level, wherein the confidence level is a probability that a target anatomical feature is present in the image frame, generating, for each processed frame, index information based on the confidence level for each frame, generating a visual representation of the index information, and causing a user interface to display the visual representation corresponding to the index information.

Any of the methods described herein, or steps thereof, may be embodied in non-transitory computer-readable medium comprising executable instructions, which when executed may cause a processor of a medical imaging system to perform the method or steps embodied herein.

BRIEF DESCRIPTION OF THE DRAWINGS

FIG. 7 is an example of how a user may interact with a visual representation of merit levels in accordance with principles of the present disclosure.

DETAILED DESCRIPTION

Figure 1:
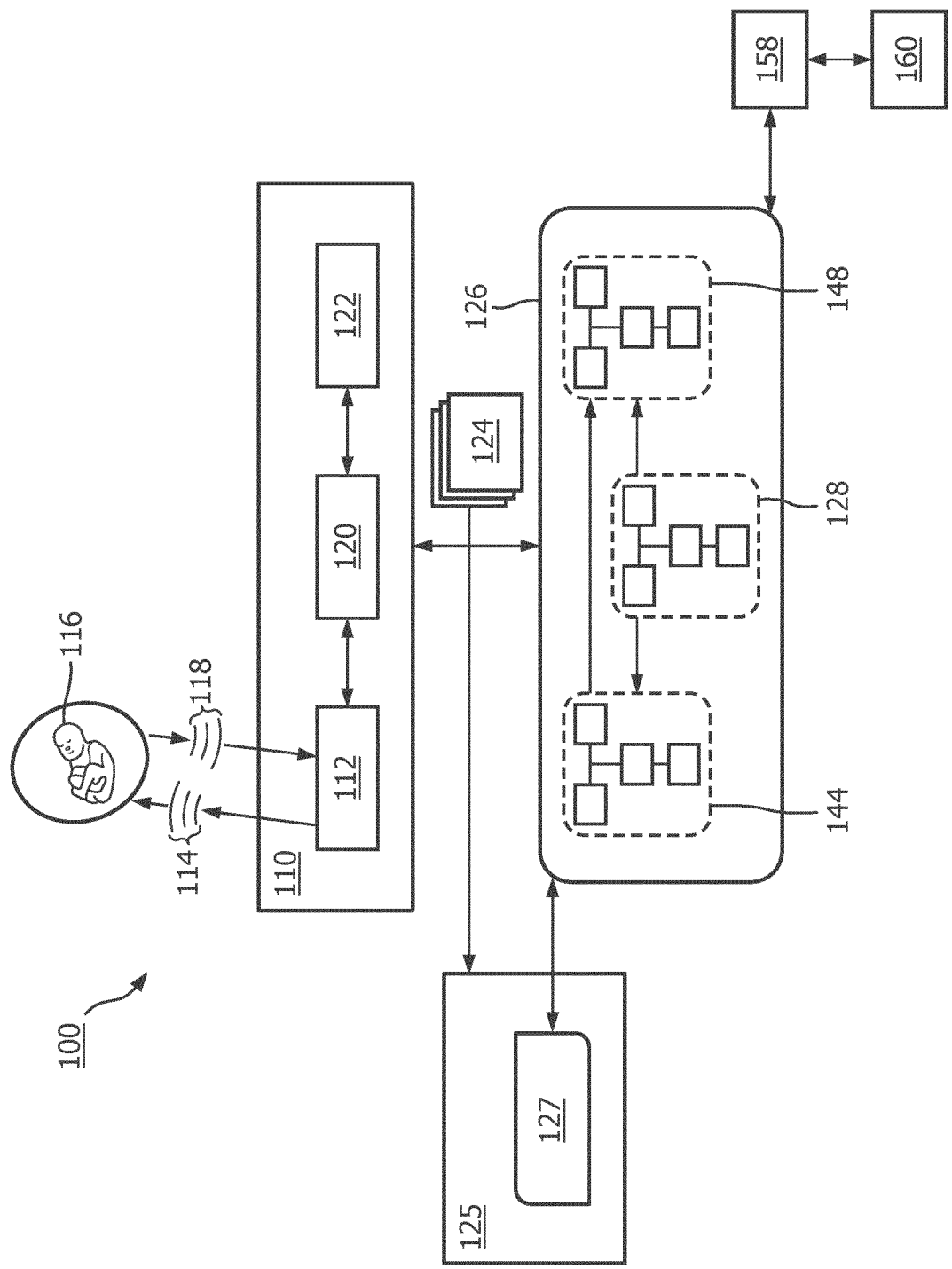
FIG. 1 is a block diagram of an ultrasound system in accordance with principles of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

During an ultrasound exam, a user may scan a region of interest of a subject with an ultrasound transducer array. The scan may acquire several planes through a volume of the region of interest. These planes may be stored as image frames of a cineloop or individual image frames. After the scan, the user may review the stored image frames to look for image frames that include acceptable images of items of interest. An item of interest may be an anatomical structure (e.g. fetal heart), a sub-feature of an anatomical structure (e.g., mitral valve), and/or it may be a particular view of an anatomical structure (e.g., four chamber view, left ventricular outflow tract) that the user wants to locate in one or more image frames. Anatomical structures and sub-features of anatomical structures the user is looking for may be referred to as target anatomical features. An image of the item of interest may be acceptable if it allows a user to make a desired measurement and/or make a diagnosis. The user may save the acceptable image frames separately from the cineloop or other image frames. In some cases, the user may save only the optimal ones of the acceptable image frames. An image frame may be optimal based on objective and/or subjective criteria (e.g., resolution, presence of other items of interest in frame, conformity of view with standard view). The user may then repeat the process for a scan of a different region of interest to acquire image frames of other items of interest. Alternatively, the user may repeat the same scan if no acceptable images were found. At the end of the ultrasound exam, some or all of the cineloops and the separately saved image frames may be stored for later review by the same or a different user. While the cineloops and other image frames may be consulted during the later review, the later review may be assisted by the preselection of the separately saved image frames during the exam. However, the iterative "scan and review" process during the exam may result in lengthy exams.

As ultrasound technology enters wider markets, new users may not have the same skill level as traditional users. These users may have limited abilities for performing scans and/or interpreting ultrasound images. During an ultrasound exam, these users may scan large regions of a subject in order to ensure one or more regions of interest are imaged. Many separate image frames and/or many and/or lengthy cineloops may be generated by these scans. These scans may be stored and provided to a separate user for review. While the ultrasound exam may be completed in a short amount of time, the review by the separate user may be lengthy as there may be hundreds or thousands of image frames to review to find acceptable images of items of interest within the regions of interest.

The technical solutions described herein may provide index information for image frames based on the presence of items of interest in the image frames. The technical solutions may also provide improved user interfaces that may allow users to quickly locate and view image frames that include items of interest. The user may store the located image frames, make measurements, and/or make a diagnosis from the located image frames. The technical solutions may provide users with data on confidence levels that items of interest are present and/or merit levels associated with the quality of image frames. In some instances, the technical solutions may automatically take anatomical measurements of items of interest in the acceptable image frames. Aspects of the index information, user interface, and/or providing of image frames may reduce the time of ultrasound exams and/or post-exam reviews. In some embodiments, the technical solutions may be implemented, at least in part, by a neural network employing deep learning algorithms.

An ultrasound system according to the present disclosure may utilize a neural network, for example a deep neural network (DNN), a convolutional neural network (CNN), a recurrent neural network (RNN), an autoencoder neural network, or the like, to determine whether an item of interest is present in each image frame of a plurality of image frames and generate a visual representation of the determinations for display. In various examples, the neural network(s) may be trained using any of a variety of currently known or later developed learning techniques to obtain a neural network (e.g., a trained algorithm or hardware-based system of nodes) that is configured to analyze input data in the form of ultrasound image frames, measurements, and/or statistics and determine whether an item of interest is present in each image frame of a plurality of image frames and generate a visual representation of the determinations (e.g., index information, confidence levels) for display.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display, in some examples, ultrasound images generated by the ultrasound imaging system. The ultrasound imaging system may include one or more processors and at least one model of a neural network, which may be implemented in hardware and/or software components. The neural network can be trained to determine whether an item of interest is present in each image frame of a plurality of image frames and generate a visual representation of the determinations for display.

The neural network implemented according to the present disclosure may be hardware—(e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a trained algorithm for determining whether one or more items of interest are present in an image frame. The ultrasound system may include a display or graphics processor, which is operable to arrange the ultrasound images (2D, 3D, 4D etc.) and/or additional graphical information, which may include annotations, index information, confidence levels, user instructions, tissue information, patient information, indicators, color coding, highlights, and other graphical components, in a display window for display on a user interface of the ultrasound system. In some embodiments, the ultrasound image frames and associated index information may be provided to a storage and/or memory device, such as a picture archiving and communication system (PACS) for post-exam review, reporting purposes, or future training (e.g., to continue to enhance the performance of the neural network), especially the image frames used to produce items of interest associated with high confidence levels. The display can be remotely located, and interacted with by users other than the sonographer conducting the imaging, in real-time or asynchronously.

As described herein, an ultrasound imaging system may include an ultrasound transducer configured to acquire echo signals responsive to ultrasound pulses transmitted toward a region of interest, one or more processors in communication with the ultrasound transducer and configured to: receive a plurality of image frames generated from the ultrasound echoes, determine, for each image frame of the plurality of image frames, whether target anatomical feature is present in the image frames, and generate, for each of the image frames of the plurality of image frames, index information based on a confidence level indicating the target anatomical feature is present in the given image frame. The ultrasound imaging system may include a user interface in communication with the one or more processors and configured to display a visual representation of the index information.

FIG. 1 shows an example ultrasound system according to principles of the present disclosure. The ultrasound system 100 may include an ultrasound data acquisition unit 110. The ultrasound data acquisition unit 110 can include an ultrasound probe which includes an ultrasound sensor array 112 configured to transmit ultrasound pulses 114 into a region 116 of a subject, e.g., abdomen, and receive ultrasound echoes 118 responsive to the transmitted pulses. The region 116 may include one or more items of interest, such as a developing fetus, as shown, or a portion of the developing fetus, such as the head or femur. Although illustrative examples may refer to fetuses or fetal anatomy, the teachings of the disclosure are not limited to fetal scans. The region 116 may include a variety of other anatomical objects or portions thereof, such as a kidney or heart, which may be items of interest. As further shown, the ultrasound data acquisition unit 110 can include a beamformer 120 and a signal processor 122, which can be configured to generate a stream of discrete ultrasound image frames 124 from the ultrasound echoes 118 received at the array 112. The ultrasound image frames 124 may be individually acquired image frames or a part of a sequence, such as a cineloop. The image frames 124 may be stored in local memory 125 of the system 100 where they may be accessed later during an exam or during post-exam review. The local memory 125 may be implemented by one or more hard disk drives, solid-state drives, or any other type of suitable storage device comprising non-volatile memory. In addition to the image frames 124, the local memory 125 may be configured to store additional image data, executable instructions, or any other information necessary for the operation of the system 100.

The image frames 124 can additionally or alternatively be communicated to a data processor 126, e.g., a computational module or circuitry, configured to determine what items of interest are present in each of the image frames 124. The data processor 126 may receive image frames 124 from the local memory 125 in some applications, for example, during post-exam review. In some examples, the data processor 126 may be configured to determine if an item of interest is present in an image frame by implementing at least one neural network, such as neural network 128, which can be trained to determine if an item of interest is present in an image frame and/or determine which image frame including an item of interest is the optimal image frame. The data processor 126 may also be configured to implement an image quality network 144 and/or an image measurement network 148 in some embodiments to increase the functionality of the data processor 126. In some embodiments, the image quality network 144 may be trained to determine which image frames including an item of interest is the optimal image frame. In some embodiments, the image measurement network 148 may be trained to obtain one or more measurements of one or more items of interest within an image frame.

In some embodiments, networks 128, 144, and/or 148 may be static learning networks. That is, the networks may be fully trained on the system 100 or another system and executable instructions for implementing the fully-trained networks 128, 144, and/or 148 are provided to the data processor 126. In some embodiments, the networks 128, 144, and/or 148 may be dynamic, continuous learning networks. In such embodiments, the executable instructions for implementing the networks 128, 144, and/or 148 are modified based on the results of each ultrasound exam. In various examples, the data processor 126 can also be coupled, communicatively or otherwise, to a database 127 configured to store various data types, including executable instructions, training data, and newly acquired, patient-specific data. In some examples, as shown in FIG. 1, the database 127 may be stored on the local memory 125, however, the database 127 may be implemented in a separate storage location on system 100.

The ultrasound data acquisition unit 110 can be configured to acquire ultrasound data from one or more regions of interest 116, which may include a fetus, other anatomy, or features thereof. The ultrasound sensor array 112 may include at least one transducer array configured to transmit and receive ultrasonic energy. The settings of the ultrasound sensor array 112 can be preset for performing a particular scan, and in embodiments, can be adjustable during a particular scan. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging. In addition to B-mode imaging, imaging modalities implemented according to the disclosures herein can also include shear-wave and/or Doppler, for example. A variety of users may handle and operate the ultrasound data acquisition unit 110 to perform the methods described herein. In some examples, the user may be an inexperienced, novice ultrasound operator unable to accurately identify each item of interest in a given scan. In some cases, the data acquisition unit 110 is controlled by a robot (positioning, settings, etc.), and can replace the human operator data to perform the methods described herein. For instance, the data acquisition unit 110 may be configured to utilize the findings obtained by the data processor 126 to refine one or more image planes and or anatomical measurements obtained therefrom. According to such examples, the data acquisition unit 110 can be configured to operate in automated fashion by adjusting one or more parameters of the transducer, signal processor, or beamformer in response to feedback received from the data processor.

The data acquisition unit 110 may also include a beamformer 120, e.g., comprising a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some embodiments, the beamformer 120 may include a microbeamformer operating on groups of sensor elements for bother transmit and receive beamforming, coupled to a main beamformer which operates on the group inputs and outputs for both transmit and receive beamforming, respectively.

The signal processor 122 may be communicatively, operatively and/or physically coupled with the sensor array 112 and/or the beamformer 120. In the example shown in FIG. 1, the signal processor 122 is included as an integral component of the data acquisition unit 110, but in other examples, the signal processor 122 may be a separate component. In some examples, the signal processor may be housed together with the sensor array 112 or it may be physically separate from but communicatively (e.g., via a wired or wireless connection) coupled thereto. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region of interest 116.

In particular embodiments, neural network 128 may comprise a deep learning network trained, using training sets of labeled imaging data, to determine if one or more items of interest are found in a given new (unknown) frame of the plurality of ultrasound image frames 124 and index the given image frame based on what items of interest are present. Information on what items of interest are in a given frame may be referred to as index information. In other words, the neural network 128 may be trained to identify one or more predetermined items of interest, and for a newly acquired image frame, the neural network 128 may determine a confidence level (e.g., probability) that an item of interest the image frame. Confidence levels for multiple items of interest may be associated with a single frame of the plurality of ultrasound image frames 124. In some embodiments, the neural network 128 may output a vector including the probabilities (e.g., confidence levels) of each item of interest which may be stored as index information and associated with the appropriate image frame by a pointer. A visual representation of which items of interest are present in each image frame may be generated by a display processor 158 and presented to a user via a user interface 160. That is, the underlying probabilities associated with each item of interest may not be displayed in a visual representation of the index information. In some embodiments, only index information associated with confidence levels above a threshold value will be displayed to the user. Additionally or alternatively, a visual representation of the underlying confidence levels associated with each image frame may be generated by a display processor 158 and presented to a user via user interface 160. In some embodiments, only confidence levels above a threshold value will be displayed to the user. The visual representation of the items of interest associated with each frame may provide the user with a visual overview as to what items of interest are present in each image frame of the plurality of ultrasound image frames 124. This may allow the user to more quickly determine which frames to review to view items of interest.

In particular embodiments, the image quality network 144 may comprise a deep learning network trained, using training sets of labeled imaging data, to generate a merit level for each of the plurality of ultrasound image frames 124 that were determined by the neural network 128 to have an item of interest present. Merit levels for multiple items of interest may be associated with a single frame of the plurality of ultrasound image frames 124. In some embodiments, a visual representation of merit levels associated with each frame for a given item of interest may be generated by the display processor 158 and presented to the user via the user interface 160. The visual representation of the merit levels associated with each frame may provide the user with a visual overview as to which image frames from the plurality of ultrasound image frames where an item of interest is present are likely to be the most appropriate for taking measurements or diagnostic purposes, for example, a standard view defined by an ultrasound exam protocol. In some embodiments, the merit levels generated by the image quality network 144 may be used to automatically present one or more image frames with the highest merit levels for an item of interest to a user via the user interface 160. In some embodiments, only image frames having a merit level above a threshold value will be displayed to the user. In some embodiments, image quality network 144 may be omitted.

In particular embodiments, the image measurement network 148 may comprise a deep learning network trained, using training sets of labeled imaging data, to generate one or more measurements for one or more items of interest present in a given frame of the plurality of ultrasound image frames 124. In some embodiments, the given frame may be selected by a user via the user interface 160. In other embodiments, the given frame may be determined based on a merit level determined by the image quality network 144. The one or more measurements generated by the image measurement network 148 may be visually presented to the user via the user interface 160. In some embodiments, image measurement network 148 may be omitted.

The outputs of neural network 128, image quality network 144, and/or image measurement network 148 may be provided to local memory 125. Outputs may include, but are not limited to, index information, confidence levels, merit levels, and measurements.

Figure 2:
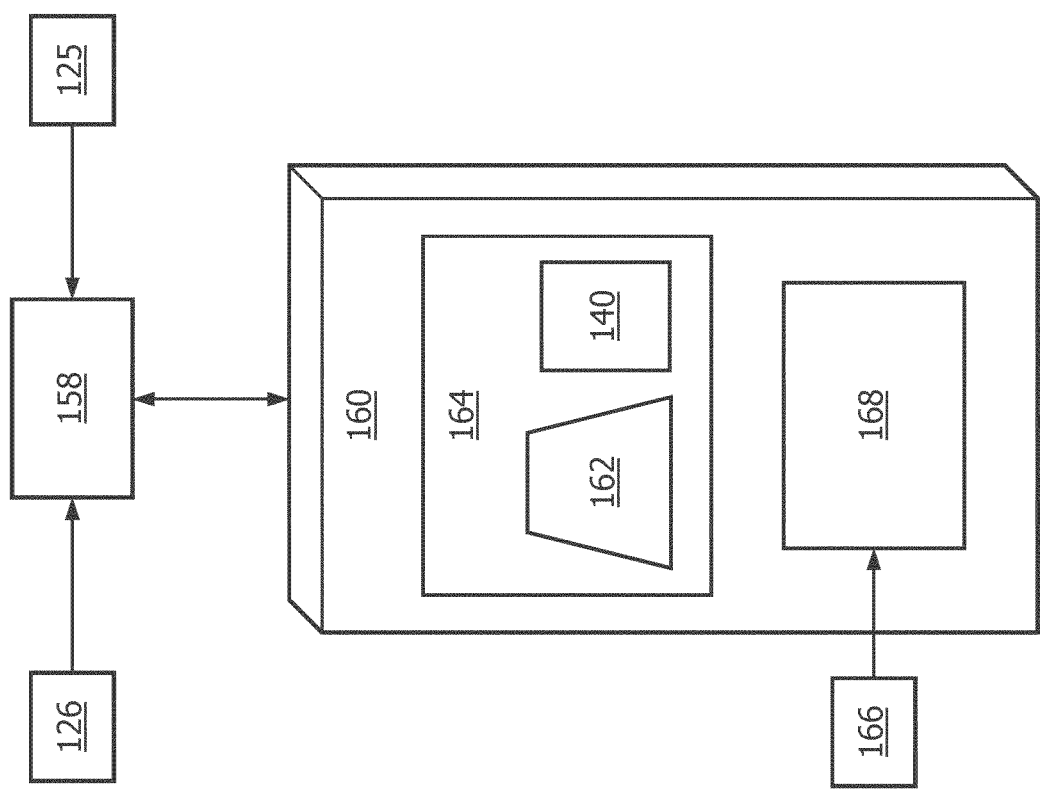
FIG. 2 is a diagram showing additional components of the ultrasound system of FIG. 1.

FIG. 2 shows additional components of the system 100. As discussed above, one or more acquired ultrasound image frames, visual representation of index information, confidence levels, merit levels, and/or measurements can be displayed to a user via one or more components of system 100. As shown in FIG. 2, such components can include a display processor 158 communicatively coupled with data processor 126. The display processor 158 is further coupled with a user interface 160, such that the display processor 158 can link the data processor 126 (and thus the one or more neural networks operating thereon) to the user interface 160, enabling the neural network outputs, e.g., visual representations of confidence levels, to be displayed on a display 164 of the user interface 160. The display 164 may include a display device implemented using a variety of known display technologies, such as LCD, LED, OLED, or plasma display technology. In embodiments, the display processor 158 can be configured to generate ultrasound images 162 from the image frames 124 received at the data processor 126 and/or local memory 125. In some examples, the user interface 160 can be configured to display the ultrasound images 162 in real time as an ultrasound scan is being performed, along with one or more visual representations 140, which may be overlaid on the images and/or displayed separately. The visual representations 140 can include index information, confidence levels, merit levels, and/or measurements in the form of annotations, color-mapping, percentages, and/or bars. Additionally, visual indications of whether all items of interest required for a particular exam (e.g., all standard views of the heart in an echocardiogram) may be provided in some embodiments. In some embodiments, user display 164 may comprise multiple displays. In some examples, the ultrasound images 162 may be displayed on a first display 164 and the visual representations 140 may be displayed on a second display 164 concurrently.

The user interface 160 can also be configured to receive a user input 166 via a user control or controls 168 at any time before, during, or after an ultrasound scan. For instance, the user interface 160 may be interactive, receiving user input 166 indicating an item of interest or a particular frame or frames of the plurality of ultrasound image frames 124 to display. In some examples, the input 166 may include an instruction to raise or lower a threshold for a confidence level or merit level or adjust one or more image acquisition settings. In some examples, the input 166 may include an indication as to an item of interest the user wishes the neural network 128 to locate in each image frame of image frames 124. In some embodiments, the user control(s) 168 may include one or more hard controls (e.g., buttons, knobs, dials, encoders, mouse, trackball or others). In some embodiments, the user control(s) 168 may additionally or alternatively include soft controls (e.g., GUI control elements or simply, GUI controls) provided on a touch sensitive display. In some embodiments, display 164 may be a touch sensitive display that includes one or more soft controls of the user control(s) 168.

The configuration of the components shown in FIG. 2, along with FIG. 1, may vary. For example, the system 100 can be portable or stationary. Various portable devices, e.g., laptops, tablets, smart phones, remote displays and interfaces, or the like, may be used to implement one or more functions of the system 100. Some or all of the data processing may be performed remotely, (e.g., in the cloud). In examples that incorporate such devices, the ultrasound sensor array 112 may be connectable via a USB interface, for example. In some examples, various components shown in FIGS. 1 and 2 may be combined. For instance, neural network 128 may be merged with the image quality network 144 and/or image measurement network 148. According to such embodiments, the output generated by neural network 128 may still be input into networks 144 and/or 148, but the three networks may constitute sub-components of a larger, layered network, for example.

Visual representations 140, provided by data processor 126 may provide an improved user interface for reviewing acquired image frames. The improved user interface may allow a user to see which frames include items of interest and reduce their review of numerous image frames to those indicated by the visual representations 140. This may increase the functionality of the system and reduce review times by users. In some embodiments, the user interface 160 may be configured to allow a user to interact with the system 100 via the visual representations 140.

Figure 3:
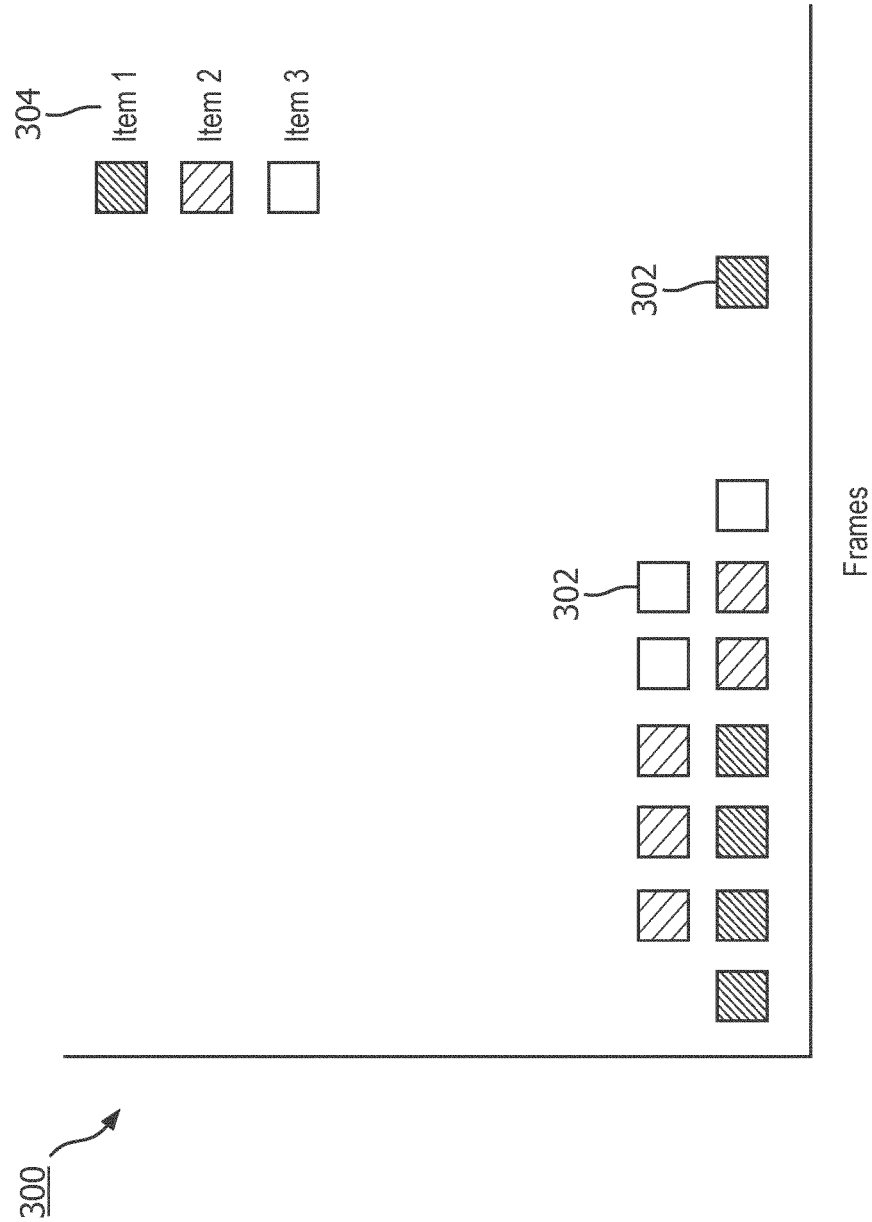
FIG. 3 is an example visual representation of index information implemented in accordance with principles of the present disclosure.

FIG. 3 illustrates an example visual representation 300 of index information according to embodiments of the disclosure. The visual representation 300 may be generated by the display processor 158 based at least in part on output from neural network 128. Visual representation 300 may be provided on a display, such as display 164 shown in FIG. 2. An example visual representation 300 may include a single graphic representing the index information for each of the analyzed frames arranged in a logical manner, for example along an axis which represents the temporal dimension of the plurality of images or in some other arrangement. In the example in FIG. 3, the horizontal axis represents the image frames in a series of individual frames and/or included in a sequence (e.g., cineloop). The horizontal axis may be labeled with the image frame number, file name of the image frame, and/or time of acquisition of the frame (not shown). For each frame, a marker 302 may indicate that one or more items of interest are present in the image frame. Thus, an example visual representation may include a plurality of markers representing the index information associated with each frame. For frames where no items of interest are present, no markers 302 may be present. Whether an item of interest is present may be based on whether an associated confidence level associated with the item of interest was above a threshold value (e.g., 90%, 80%, 70%, 50%). The threshold value may be pre-set in the system (e.g., system 100) or may be indicated by a user input (e.g. input 166). The visual representation 300 may further include a legend 304 indicating which markers correspond to which items of interest. In the example illustrated in FIG. 3, three different items of interest are indicated, but it is understood that any number of items of interest may be indexed. Furthermore, although the markers 302 are shown as boxes in FIG. 3, other marker types may be used (e.g., bars, stars, circles, crosses). The markers for different items of interest may be differentiated by color, shape, size, and/or other visual properties. The markers 302 may allow a user to quickly see which image frames include particular items of interest.

Figure 4:
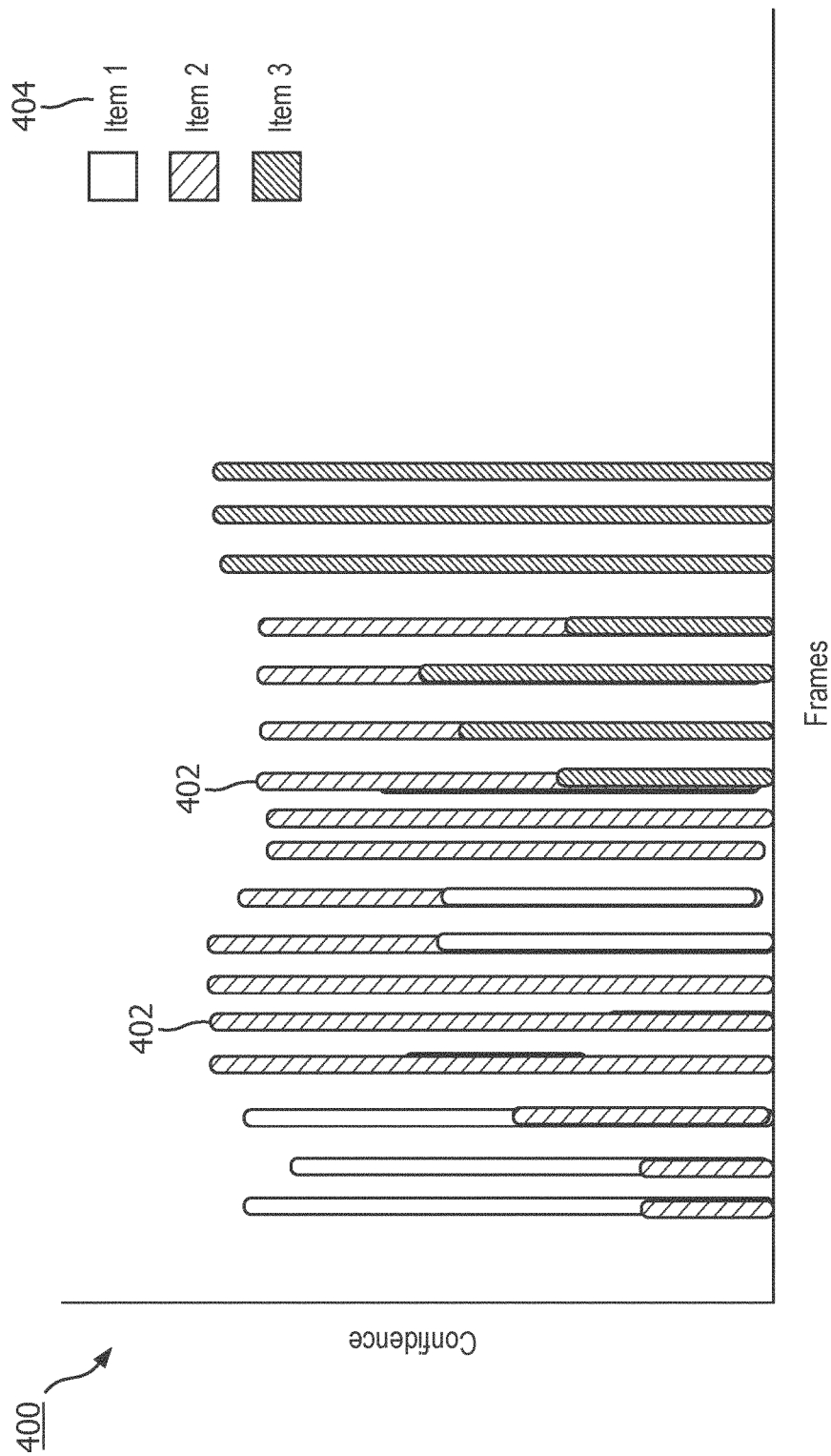
FIG. 4 is an example visual representation of confidence levels implemented in accordance with principles of the present disclosure.

While the example visual representation 300 of index information shown in FIG. 3 may allow a user to quickly view which image frames contain which items of interest, in some applications, a user may wish to view the underlying confidence levels used to generate the index information. FIG. 4 illustrates an example visual representation 400 of confidence levels according to embodiments of the disclosure. The visual representation 400 may be generated by the display processor 158 based at least in part on output from neural network 128. Visual representation 400 may be provided on a display, such as display 164 shown in FIG. 2. An example visual representation 400 may include a single graphic representing the confidence levels for each of the analyzed frames arranged in a logical manner. For example, the confidence levels may be plotted relative to a first axis which represents the magnitude of the confidence level and the frames may be arranged along a second axis which represents the temporal dimension of the plurality of images or in some other arrangement. As in FIG. 3, the horizontal axis represents the image frames in a series of individual frames and/or included in a sequence (e.g., cineloop). The horizontal axis may be labeled with the image frame number, file name of the image frame, and/or time of acquisition of the frame (not shown). The vertical axis represents the confidence level (e.g., a probability between 0-100%) that a given item of interest is present in an image frame. For each frame, one or more markers 402 may indicate a confidence level that one or more items of interest are present in the frame. A visual characteristic of the markers 402 may vary based on the confidence level. As shown in the example in FIG. 4, markers 402 are in the form of bars with heights (e.g., the visual characteristic) corresponding to the confidence level are provided for each frame. The visual characteristic or an additional visual characteristic of the markers 402 may vary based on the item of interest associated with the confidence level. In the example shown, bars of different shades associated with different items of interest are overlaid on top of one another if more than one item of interest is present in the frame. Other marker types and/or visual characteristics may be used to represent the confidence level and/or item of interest. For example, the markers 402 could be squares having different colors representative of the confidence level, and an overlay pattern (e.g., stripes, dots, crosshatch) on the squares could indicate the item of interest. Frames where there is no confidence that any item of interest is present may not have a marker. In some embodiments, confidence levels below a certain threshold (e.g., 90%, 80%, 70%, 50%) may not be shown. The threshold may be pre-set in a system (e.g., system 100) or may be indicated by a user via a user input (e.g., input 166). The visual representation 400 may further include a legend 404 indicating which markers correspond to which items of interest. The markers 402 may allow a user to quickly see which image frames are most likely to include particular items of interest.

A user may interact with a visual representation of index information, confidence levels, merit levels, and/or measurements via a user interface (e.g., user interface 160). The user may provide an input (e.g., user input 166) via a user control (e.g., user control 168). For example, the user interface may include a selector that is used to select an item of interest, an image frame, and/or a visual representation of other outputs from the visual representation by selecting a marker, an image frame number labeled on an axis, and/or an item in a legend. In some embodiments, the selector may be generated by a display processor (e.g., display processor 158) and provided on a display (e.g., display 164). The user may control the selector via the user control (e.g., track ball, mouse, touch screen). In some embodiments, image frames and/or other visual representations may be provided automatically on the display based on the user's inputs. For example, a user may select an item of interest and the system may automatically display the image frame having the highest merit level for the item of interest. Interaction with the visual representation, such as with a selector, may allow a user to quickly locate and visualize desired image frames, thus reducing review time.

Figure 5:
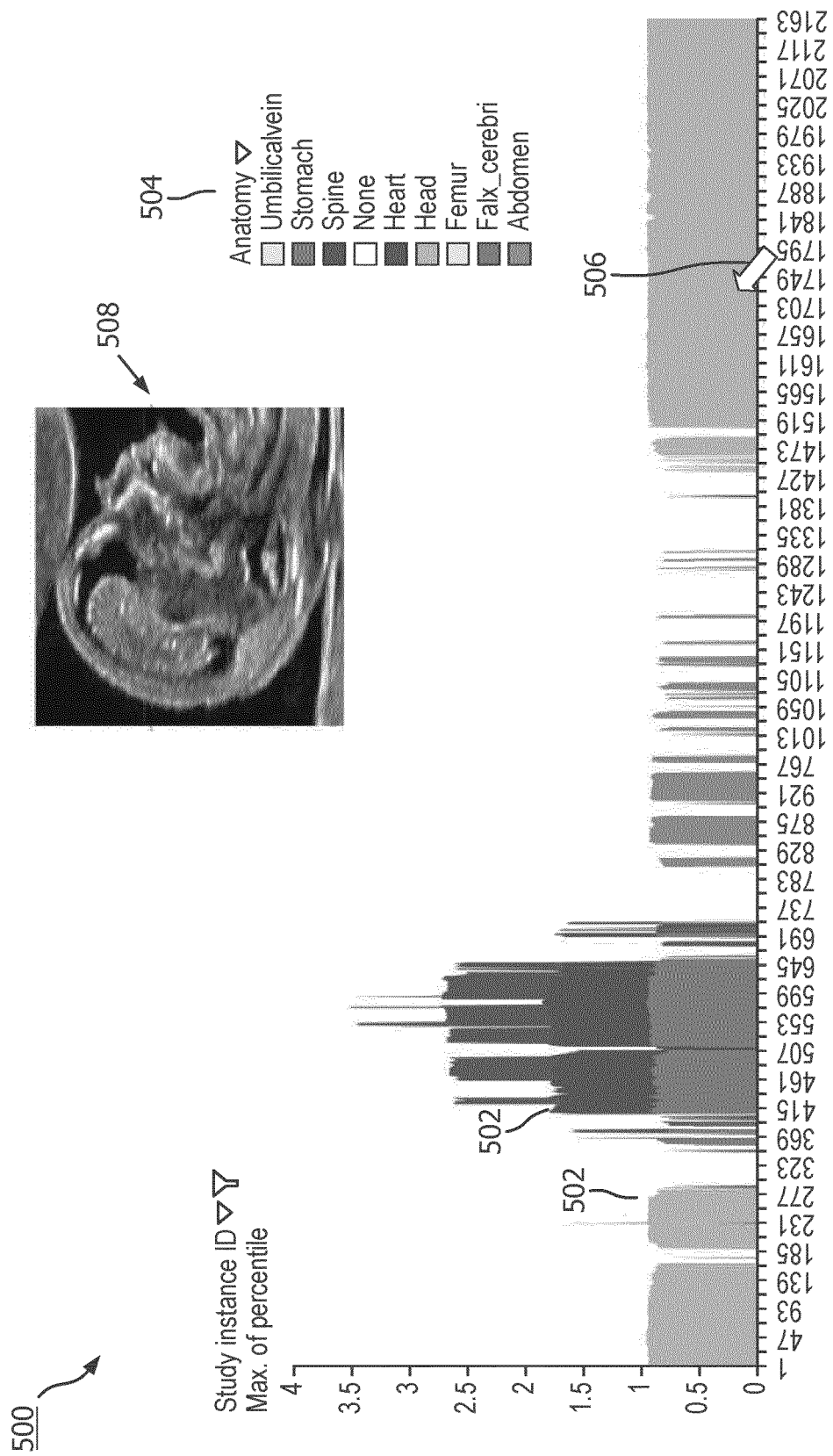
FIG. 5 an example of how a user may interact with a visual representation of confidence levels in accordance with principles of the present disclosure.

FIG. 5 illustrates an example of how a user may interact with a visual representation, such as visual representation 500 of confidence levels. The visual representation 500 may be generated by the display processor 158 based at least in part on output from neural network 128. The visual representation 500 may be provided on a display, such as display 164 shown in FIG. 2. The visual representation 500 may be similar to visual representation 400 of confidence levels. The visual representation 500 includes a horizontal axis and a vertical axis. The horizontal axis labeled with image frame numbers 501. The image frame numbers 501 may indicate the frame number in a cineloop or in a file of image frames. The vertical axis is labeled with the confidence level. For each image frame where one or more items of interest are present, one or more markers 502 in the form of bars with heights indicating the confidence level are displayed. A different color bar is provided for each item of interest. Visual representation 500 further includes a legend 504 indicating which colors are associated with which items of interest. In the example illustrated in FIG. 5, the items of interest are various fetal anatomical features (e.g., umbilical cord, stomach, spine).

As shown in FIG. 5, a user may interact with the visual representation 500 by providing an input (e.g., user input 166) via a user control, such as user controls 168 shown in FIG. 2. The user may control the location of a selector 506 via the user controls (e.g., trackball, mouse, arrow keys, touch screen). The selector 506 may be placed over a marker 502 associated with a particular frame. In response to the input (e.g., placement of the selector 506), the user interface may provide the corresponding image frame 508 on a display. As shown in the example in FIG. 5, the selector 506 is placed on a marker 502 associated with a frame where a fetal head has been determined to be present. The input by the user may be provided to the data processor 126 and a corresponding image frame 508 from image frames 124 may be provided by the data processor 126 to display processor 158 which may display image frame 508 above the visual representation 500. Alternatively, display processor 158 may retrieve the image frame 508 for display based on the user input without assistance from data processor 126. The user interface 160 may further be configured to provide the same output if the selector 506 is placed on a frame number 501 along the horizontal axis. Once an image frame is displayed, the user may then provide one or more additional inputs including, but not limited to, saving the selected image frame to memory (e.g., local memory 125), making measurements on the selected image frame, and moving the selector 506 to view a different frame. In some embodiments, the user may select to view multiple image frames simultaneously. While illustrated as an arrow in the example shown in FIG. 5, the selector 506 may be displayed as another appropriate indicator (e.g., crosshairs, triangle). In some embodiments, the selector 506 may not be displayed. For example, the visual representation 500 may be displayed on a touch screen and the user's touch may indicate the location of the selector.

A user interface configured to display image frames based on an input from a user interacting with a visual representation may allow the user to quickly image frames where a desired item of interest is present. This may be less cumbersome than if the user viewed the visual representation and then manually searched for the image frames in a file folder or scrolled through the image frames in a cineloop.

Although the example illustrated in FIG. 5 shows the image frame 508 and visual representation 500 displayed together, the image frame 508 and visual representation 500 may be provided on different displays. For example, the visual representation 500 may be provided on a touch screen of an imaging system and the image frame 508 may be provided on a main viewing screen of the system.

Figure 6A:
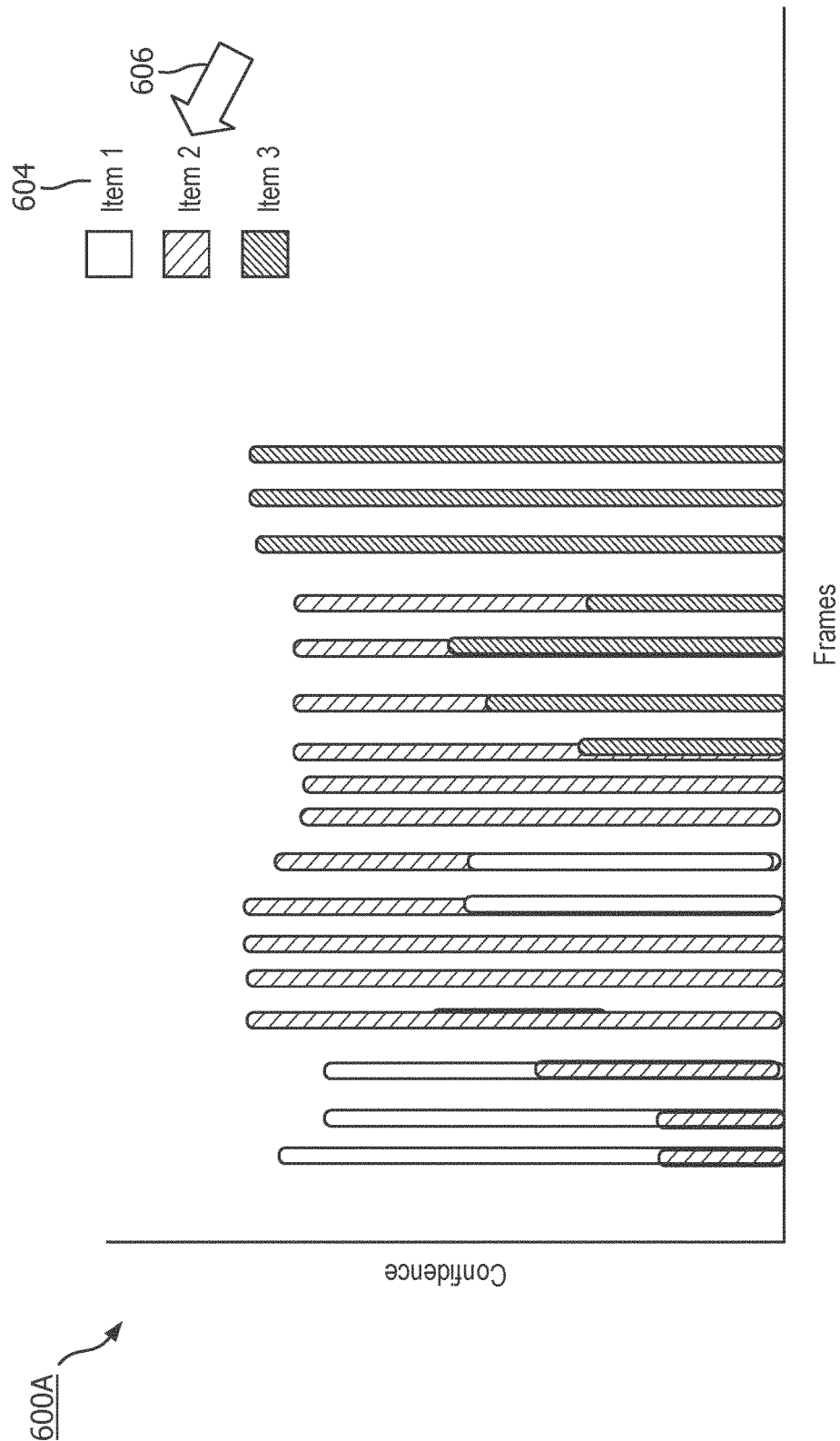
FIG. 6A an example of how a user may interact with a visual representation of confidence levels in accordance with principles of the present disclosure.
Figure 6B:
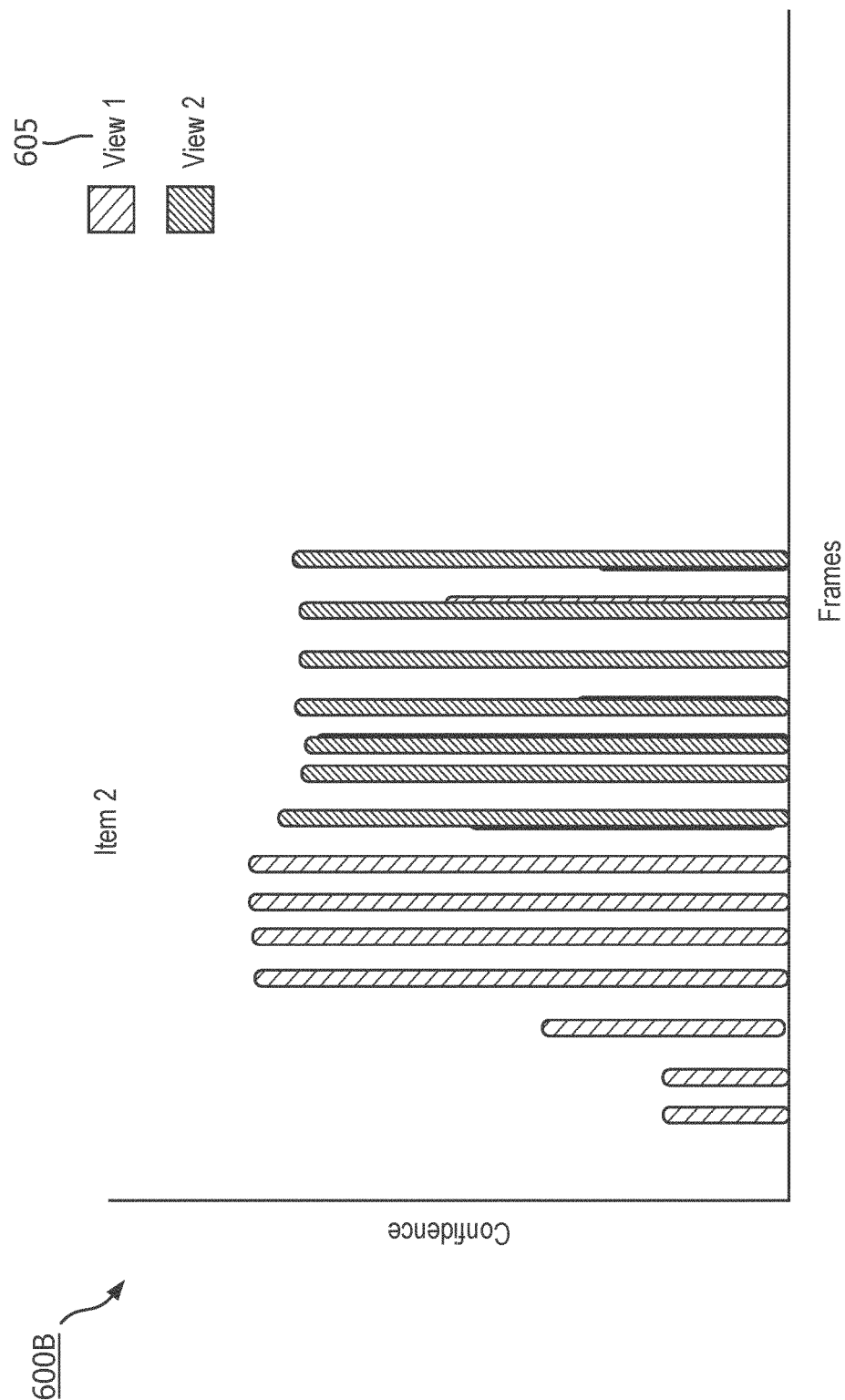
FIG. 6B an example of how a user may interact with a visual representation of confidence levels in accordance with principles of the present disclosure.

FIGS. 6A and 6B illustrates another an example of how a user may interact with a visual representation, such as visual representations 600A and 600B of confidence levels. As shown in 6A, a user may use a selector 606 to choose an item of interest from a legend 604. The user may then be provided with visual representation 600B shown in FIG. 6B. Visual representation 600B displays confidence levels for the presence of different sub-features 605 of Item 2. In the example shown in FIG. 6B, the sub-features 605 are different views of Item 2. The different views may be standard views associated with a particular type of ultrasound exam (e.g., four-chamber view of the heart) or anatomical features of a larger structure (e.g., a particular vertebra of the spine). Similar to the example shown in FIG. 5, the user may then select an image frame to view from the visual representation 600B.

After a user selects an item of interest from visual representation 600A, the user may be provided with visual representation 700 as shown in the example illustrated in FIG. 7. Visual representation 700 may be provided instead of or in addition to visual representation 600B. In contrast to visual representation 600B of confidence levels, the vertical axis represents the merit level of an item of interest present in the image frame or a sub-feature of an item of interest present in the frame. As will be discussed in more detail below, the merit level may be a measure of the quality of the image (e.g., resolution, conformity with a standard view). Visual representation 700 may be generated by display processor 158 based at least in part on output from image quality network 144. For appropriate frames (e.g., where a sub-feature is present), a marker 702 may indicate a merit level for one or more items of interest or sub-features thereof. In the example shown in FIG. 7, as indicated by legend 704, markers 702 are in the form of bars with heights corresponding to the merit levels of two different views of Item 2 are provided for appropriate frames. In some embodiments, merit levels below a certain threshold (e.g., 90%, 80%, 70%, 50%) may not be shown. The threshold may be pre-set in a system (e.g., system 100) or may be indicated by a user via a user input (e.g., input 166). Similar to the example shown in FIG. 5, the user may then select an image frame to view from the visual representation 700. Alternatively, data processor 126 may automatically provide image frames 708 and 710 associated with the highest merit levels for each view for display. In the example shown in FIG. 7, Views 1 and 2 correspond to two standard cardiac views: a four-chamber view of a heart (image frame 708) and a left ventricular outflow tract (image frame 710).

In some embodiments, when a user selects an item of interest from visual representation 600A, rather than providing a visual representation of the merit levels for each view, the data processor 126 may provide the image frame with the highest merit level for each view for display. For example, image frames 708 and 710 may be provided without any visual representation of the corresponding merit levels. In some embodiments, such as those where image quality network 144 is omitted, when a user selects an item of interest from a visual representation of index information and/or confidence levels, the data processor 126 may provide the image frame or frames with the highest confidence level.

Figure 8:
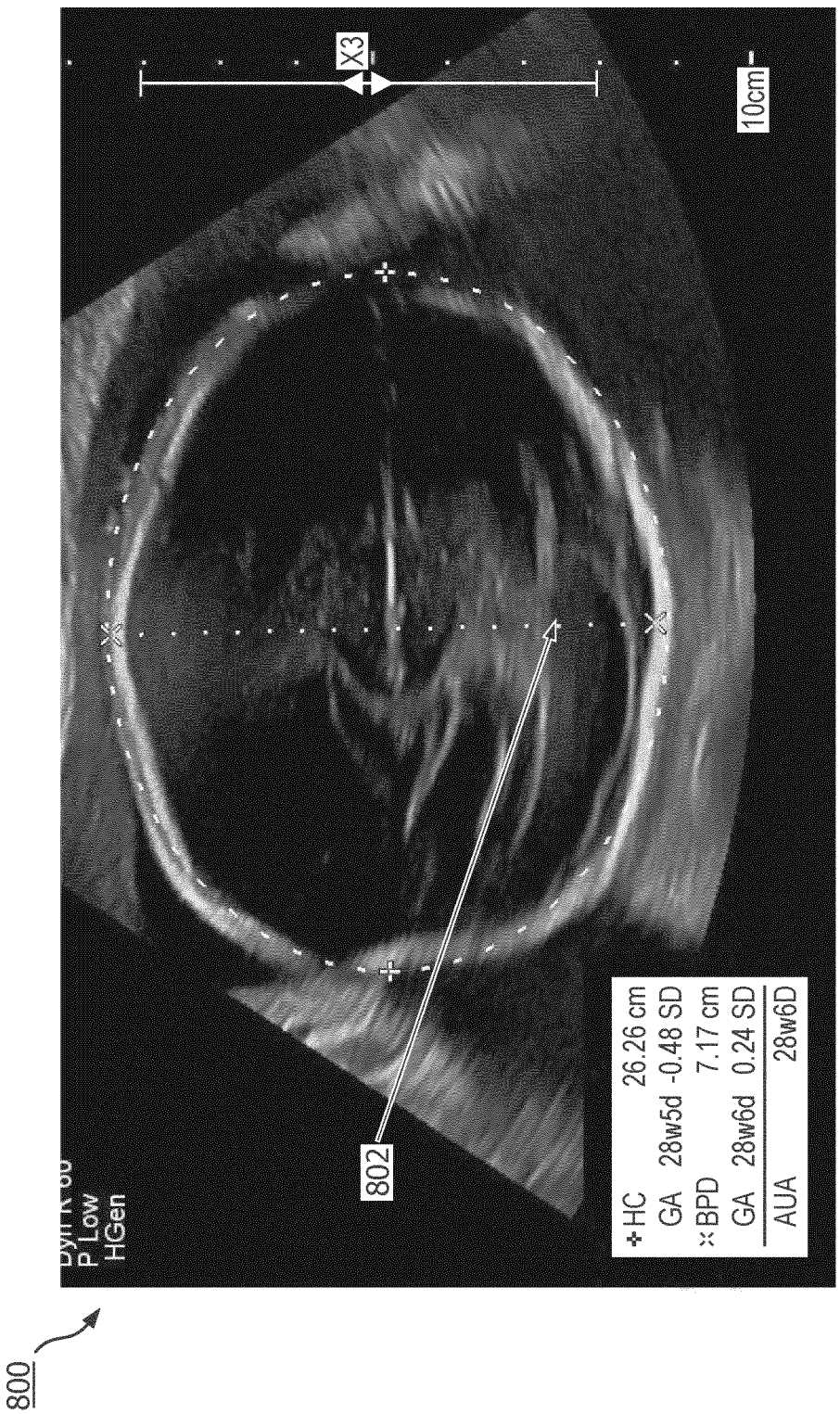
FIG. 8 is an example of acquiring a measurement of an item of interest in accordance with principles of the present disclosure.

As discussed above, once an image frame is displayed, a user may make measurements on the displayed image (e.g., image frames 708 and/or 710 shown in FIG. 7). In some embodiments, the data processor 126 may automatically acquire measurements of one or more items of interest in an image frame. For example, as shown in FIG. 8, the image measurement network 148 may acquire a biparietal diameter 802 of a fetal skull from image frame 800. The measurements (e.g., diameter 802) may be stored as annotations of image frame 800 in local memory 125. The image frame 800 may be selected based on a merit level, that is, an output of image quality network 144. For example, the image frame with the highest merit level for an appropriate view of the skull for obtaining the biparietal diameter. In some embodiments, a user may determine which image frame is used by the image measurement network 148. Image frame 800 may or may not be shown on a display during acquisition of the measurements.

The user interactions with the visual representations generated by system 100 in reference to FIGS. 5-8 are provided as examples, but principles of the present disclosure are not limited to the examples provided herein as many other interactions are possible. For example, when a user selects an item of interest, the system may generate a cineloop consisting of only those image frames where the item of interest is present based on an output of neural network 128. As a further example, when a user selects an item of interest, image frames with the highest merit levels and/or confidence levels may be displayed for each period of time (e.g., 1 second, 10, seconds, 30 seconds, 1 minute) based on outputs of neural network 128 and/or image quality network 144.

Figure 9:
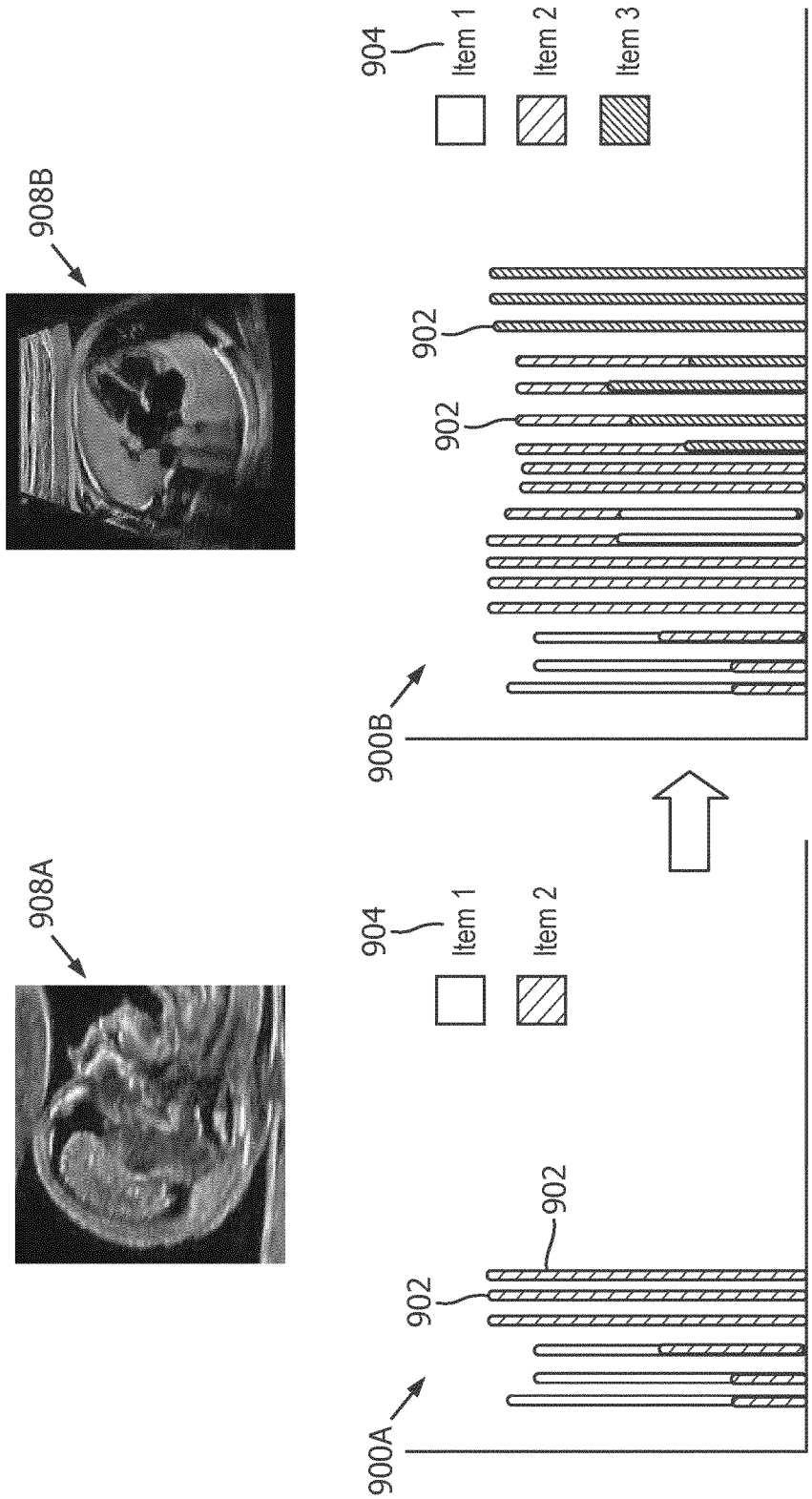
FIG. 9 is an example of a dynamic visual representation of confidence levels in accordance with principles of the present disclosure.

Visual representations described herein may be dynamically generated and displayed in real time. That is, indexing information, confidence levels, merit levels, and/or measurements may be determined in real time and visual representations of those determinations may be provided to a user during image acquisition. As shown in the example illustrated in FIG. 9, an initial visual representation 900A for a scan including image frame 908A is displayed. As additional image frames, such as image frame 908B, are acquired during an ultrasound exam, visual representation 900A is updated as shown in visual representation 900B to include markers 902 indicating confidence levels for each image frame as it is acquired. Additional items of interest are also added to the legend 904 as they are located.

Dynamically updating a visual representation of index information, confidence levels, and/or merit levels may allow a user performing an ultrasound exam to see what items of interest have been acquired. A user interface configured to provide confidence and/or merit levels may allow the user to confirm that adequate images of items of interest or views of said items have been acquired. This may be beneficial especially when the user is a less skilled ultrasound user.

In some embodiments, a legend of a visual representation may already include a list of all items of interest required to be imaged during the exam prior to beginning acquisition. The list may be based on the standard views required for a type of exam or the list may be based on user input provided via a user interface. The visual representation may provide an indication (e.g., checkmark, highlight) as each required item of interest is acquired. In some embodiments, the indication will not be provided unless an image of an item of interest is acquired that has a confidence level and/or merit level above a threshold. The threshold may be preset in the system or determined by a user.

Although the examples provide above for items of interest have included static features such as anatomical structures or portions thereof, items of interest may include dynamic features, for example, a jet of flow from a heart valve or a premature ventricular contraction. For some dynamic features (e.g., QRS complex), index information may link multiple image frames in a sequence to indicate which image frames include the dynamic feature of interest. For other dynamic features (e.g., peak flow), the index information may be associated with a single image frame.

As discussed previously, the visual representations described in reference to FIGS. 3-9 may be generated by data processor 126, which may include one or more neural networks. In some embodiments, the system 100 can be configured to implement neural network 128, which may include a CNN, to determine items of interest present in a given image frame. The items of interest in a given image frame may be provided as index information. As discussed previously in reference to FIG. 1, neural network 128 may base the index information on a determination that a probability that one or more items of interest are present in the given image frame is above a threshold. The neural network 128 may return only the items of interest determined to be present based on the probability (e.g., index information) or the neural network 128 may further return the associated probabilities (e.g., confidence levels). Neural network 128 may return a separate confidence level for each item of interest as a data structure, such as a vector. In some embodiments, a pointer may link each vector to an appropriate image frame. The index information and/or confidence levels may be generated based on image data provided to neural network 128, such as image data included in image frames 124. The neural network 128 may be trained with imaging data such as image frames where one or more items of interest are labeled as present. Neural network 128 may be trained to recognize target anatomical features associated with standard ultrasound exams (e.g., different standard views of the heart for echocardiography) or a user may train neural network 128 to locate one or more custom target anatomical features (e.g., implanted device, liver tumor).

In some embodiments, the system 100 can be configured to implement a neural network to determine the quality of image frames where an item of interest is present. The level of quality may be provided as a merit level. The merit level may be based, at least in part, on outputs from neural network 128. In particular, an image quality network 144, which may comprise a CNN, can be trained to determine whether a given ultrasound image contains the requisite anatomical landmarks for obtaining a particular measurement and/or standard view. In some examples, these landmarks may be other items of interest and/or sub-features of an item of interest. For example, biparietal diameter and head circumference measurements may be erroneous if the transthalamic view is not obtained with the ultrasound probe. In the transthalamic view, the thalami and cavum septum pellucideum should both be visible. Similarly, the abdominal circumference measurement may be erroneous if the stomach, umbilical vein, and two ribs on each side of the abdomen are not visible. Accordingly, when biparietal diameter and head circumference measurements are sought, the image quality network 144 can be configured to determine whether the thalami and cavum septum pellucideum are included in image frames indicated by the neural network 128 to include a head. Likewise, when the abdominal circumference is sought, the image quality network 144 can be configured to determine whether the stomach, umbilical vein, and two ribs on each side of the abdomen are included in image frames indicated by the neural network 128 to include the stomach, umbilical vein, and/or a rib. By confirming the presence of one or more landmarks required for a standard view and/or measurement based on the output of neural network 128, the image quality network 144 may generate a merit level based on the probability that the correct imaging plane for a specified anatomical measurement and/or standard view is included in an image frame. The probability may be based, at least in part, on the confidence levels for each of the landmarks (e.g., items of interest, sub-features) generated by the neural network 128.

In some embodiments, image quality network 144 can be trained to determine whether a given ultrasound image is of high, low or medium quality. The inputs received by the image quality network 144 can include ultrasound images and/or image settings, such as frequency, gain, etc. Inputs can also include quality measures such as an aberration estimate that degrades image quality, image resolution, and/or a noise estimate obtained via frequency. The image quality network 144 can be trained with a plurality of images, each image correlated with the aforementioned inputs and labeled as having various levels of quality. One or more quality measures may be used to further compute or weight the merit level. For example, if two image frames have the same probability that a standard view is present, the two images may have different merit levels if the two frames have different image quality (e.g., image frame has higher noise due to poor acoustic coupling during acquisition).

In some embodiments, neural network 128 may be further trained to determine whether all landmarks required for a measurement and/or standard view are present in an image frame and provide index information and/or confidence level information for these image frames to the image quality network 144. Image quality network may then only analyze quality measures of the image frames to generate merit levels. In some embodiments, the merit level may be a categorical output (e.g., high, medium, low) rather than a numerical output.

In various embodiments, the merit levels of the image quality network 144 can be utilized as another input source processed by image measurement network 148. The image measurement network 148 may be configured to only make measurements on image frames having a merit level above a threshold level (e.g., 95%, 90%, 80%). This may reduce the probability that erroneous measurements will be obtained by measurement network 148.

In some examples, a neural network training algorithm associated with the neural network 128, 144 and/or 148 can be presented with thousands or even millions of training data sets in order to train the neural network to determine a confidence level for each measurement acquired from a particular ultrasound image. In various examples, the number of ultrasound images used to train the neural network(s) may range from about 50,000 to 200,000 or more. The number of images used to train the network(s) may be increased if higher numbers of different items of interest are to be identified, or to accommodate a greater variety of patient variation, e.g., weight, height, age, etc. The number of training images may differ for different items of interest or features thereof, and may depend on variability in the appearance of certain features. For example, tumors typically have a greater range of variability than normal anatomy. Training the network(s) to assess the presence of items of interest associated with features for which population-wide variability is high may necessitate a greater volume of training images.

Figure 10:
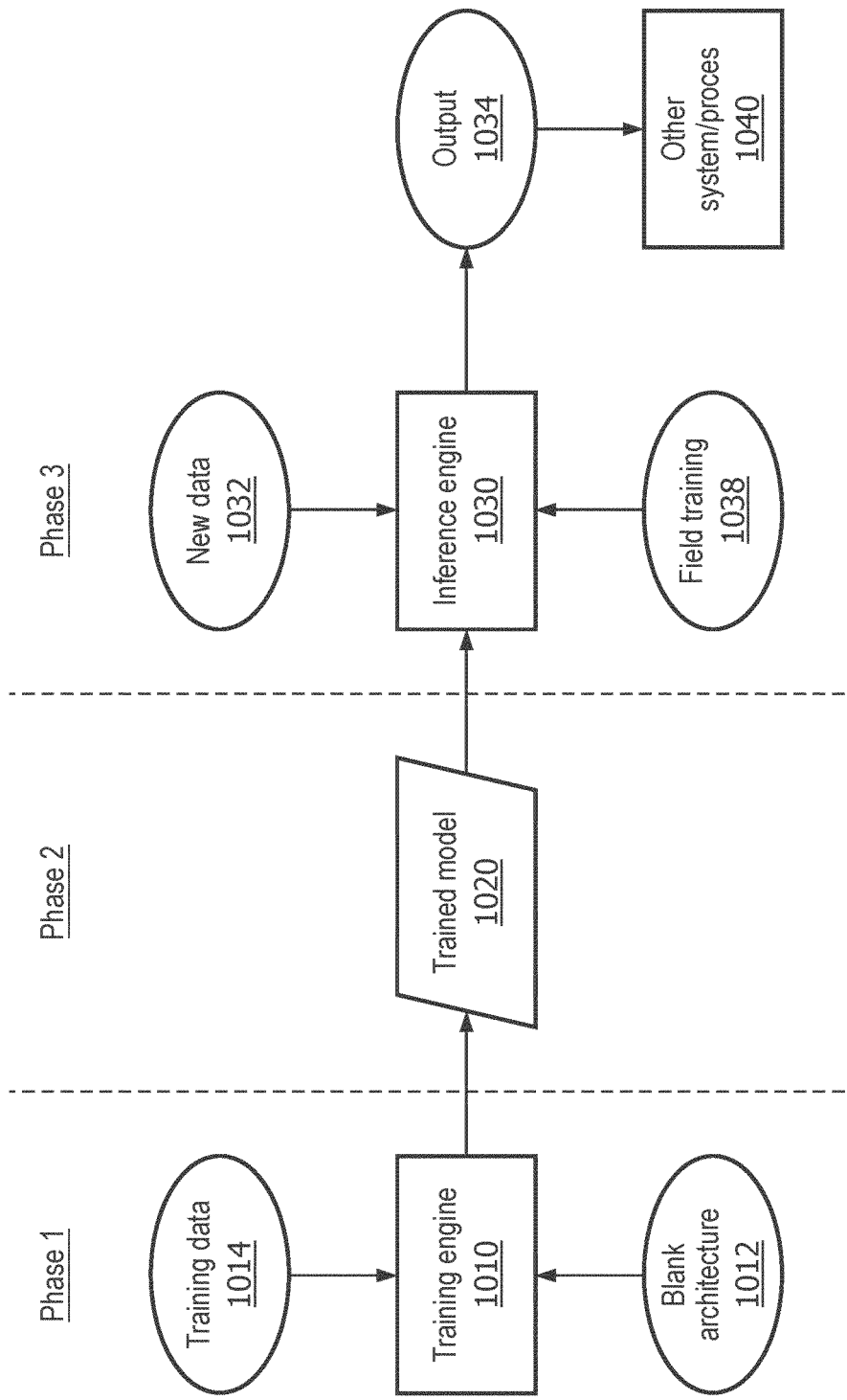
FIG. 10 shows a methodology for training and deploying an artificial neural network (or machine-learning model) in an ultrasound imaging system in accordance with the present disclosure.

FIG. 10 shows a block diagram of a process for training and deployment of a neural network in accordance with the principles of the present disclosure. The process shown in FIG. 10 may be used to train networks 128, 144, and/or 148.

The left hand side of FIG. 10, phase 1, illustrates the training of a neural network. To train neural network 128, 144 and/or 148, training sets which include multiple instances of input arrays and output classifications may be presented to the training algorithm(s) of the neural network(s) (e.g., AlexNet training algorithm, as described by Krizhevsky, A., Sutskever, I. and Hinton, G. E. *"ImageNet Classification with Deep Convolutional Neural Networks,"* NIPS 2012 or its descendants). Training may involve the selection of a starting network architecture 1012 and the preparation of training data 1014. The starting network architecture 1012 may be a blank architecture (e.g., an architecture with defined layers and arrangement of nodes but without any previously trained weights) or a partially trained network, such as the inception networks, which may then be further tailored for classification of ultrasound images. The starting architecture 1012 (e.g., blank weights) and training data 1014 are provided to a training engine 1010 for training the model. Upon sufficient number of iterations (e.g., when the model performs consistently within an acceptable error), the model 1020 is said to be trained and ready for deployment, which is illustrated in the middle of FIG. 10, phase 2. The right hand side of FIG. 10, or phase 3, the trained model 1020 is applied (via inference engine 1030) for analysis of new data 1032, which is data that has not been presented to the model during the initial training (in phase 1). For example, the new data 1032 may include unknown images such as live ultrasound images acquired during a scan of a patient (e.g., image frames 124 in FIG. 1). The trained model 1020 implemented via engine 1030 is used to classify the unknown images in accordance with the training of the model 1020 to provide an output 1034 (e.g., item of interest present in an image frame, confidence level item of interest is present, merit level of image frame). The output 1034 (e.g., type of biological tissue) may then be used by the system for subsequent processes 1040 (e.g., as input to one or more other machine-learning models, and for effecting an action by the system such as automatically displaying an image frame with the highest merit level).

In the examples where the trained model 1020 is used to implement neural network 128, the starting architecture may be that of a convolutional neural network, or a deep convolutional neural network, which may be trained to perform image frame indexing, image segmentation, image comparison, or any combinations thereof. With the increasing volume of stored medical image data, the availability of high-quality clinical images is increasing, which may be leveraged to train a neural network to learn the probability of a given image frame containing a given item of interest (e.g., confidence level). The training data 1014 may include multiple (hundreds, often thousands or even more) annotated/labeled images, also referred to as training images. It will be understood that the training image need not include a full image produced by an imagining system (e.g., representative of the full field of view of the probe) but may include patches or portions of images of the labeled item of interest.

In various embodiments, the trained neural network 128, image classification network 144 and/or image quality network 148 may be implemented, at least in part, in a computer-readable medium comprising executable instructions executed by a processor, e.g., data processor 126.

Figure 11:
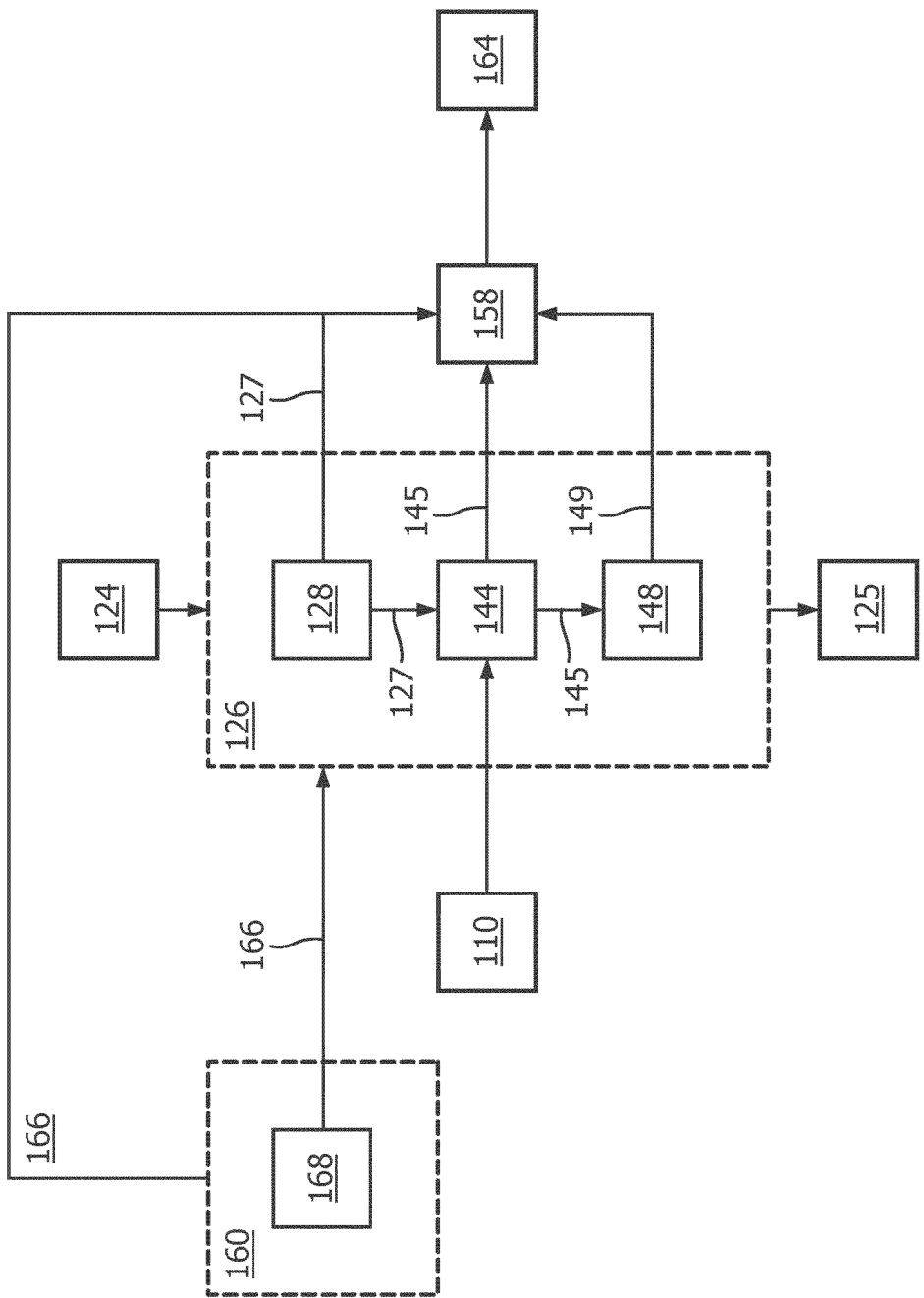
FIG. 11 is a flow diagram of inputs and outputs of a data processor in accordance with principles of the present disclosure.

As discussed with reference to FIGS. 5-9, the visual representations 140 are generated based at least in part on outputs from the data processor 126, which may be based on outputs of neural network 128, image quality network 144, and/or measurement network 148 and users may interact with the system 100 via the visual representations 140. FIG. 11 shows a flow diagram of inputs and outputs into the data processor 126. As discussed with reference to FIG. 1, data processor 126 may include neural network 128, image quality network 144, and image measurement network 148. Neural network 128 may receive acquired ultrasound image frames 124 as input. Based on this input, neural network 128 may output index information and/or confidence levels 127 for items of interest present in each image frame 124. These outputs 127 may be provided to the display processor 158 for generating a visual representation of the outputs. Neural network 128 may further receive a user input 166 via a user control 168 of the user interface 160. The user input 166 may define what items of interest the neural network 128 should index and/or a minimum confidence level required.

The index information and/or confidence levels 127 output by neural network 128 may be provided to image quality network 144. Image quality network 144 may use these outputs 127 to determine which image frames of image frames 124 to use as inputs. In some embodiments, image quality network 144 may further receive inputs from data acquisition unit 110. Inputs from data acquisition unit 110 may include acquisition settings (e.g., power, frequency) that may affect quality measures. Based on the inputs, image quality network 144 may output merit levels 145 to display processor 158 for generating a visual representation of the merit levels.

The merit levels 145 output by image quality network 144 may be provided to image measurement network 148. Image measurement network 148 may use the merit levels 145 to determine which image frames of image frames 124 to use as inputs. In some embodiments, image measurement network 148 may further receive a user input 166 indicating which measurements are desired. Based on the inputs, image measurement network 148 may output one or more measurements 149 for one or more items of interest in the image frames. The measurements may be provided to display processor 158 for generating a visual representation of the measurements. The measurements may also or alternatively be provided to local memory 125.

Display processor 158 may use the outputs 127, 145, and 149 of networks 128, 144, and 148 to generate visual representations of the indexing information, confidence levels, merit levels, and/or measurements. The visual representations may be output to the display 164. In some embodiments, a user input 166 from interacting with the visual representation via the user interface 160 (e.g., via a selector controlled by user control 168) may be provided to the display processor 158. The user input 166 may be used to change the visual representation provided to display 164 and/or what image frame from image frames 124 is provided to display 164. Alternatively, user input 166 is provided to data processor 126, and data processor 126 provides updated outputs to display processor 158 to determine the visual representation and image frame provided to display 164.

Figure 12:
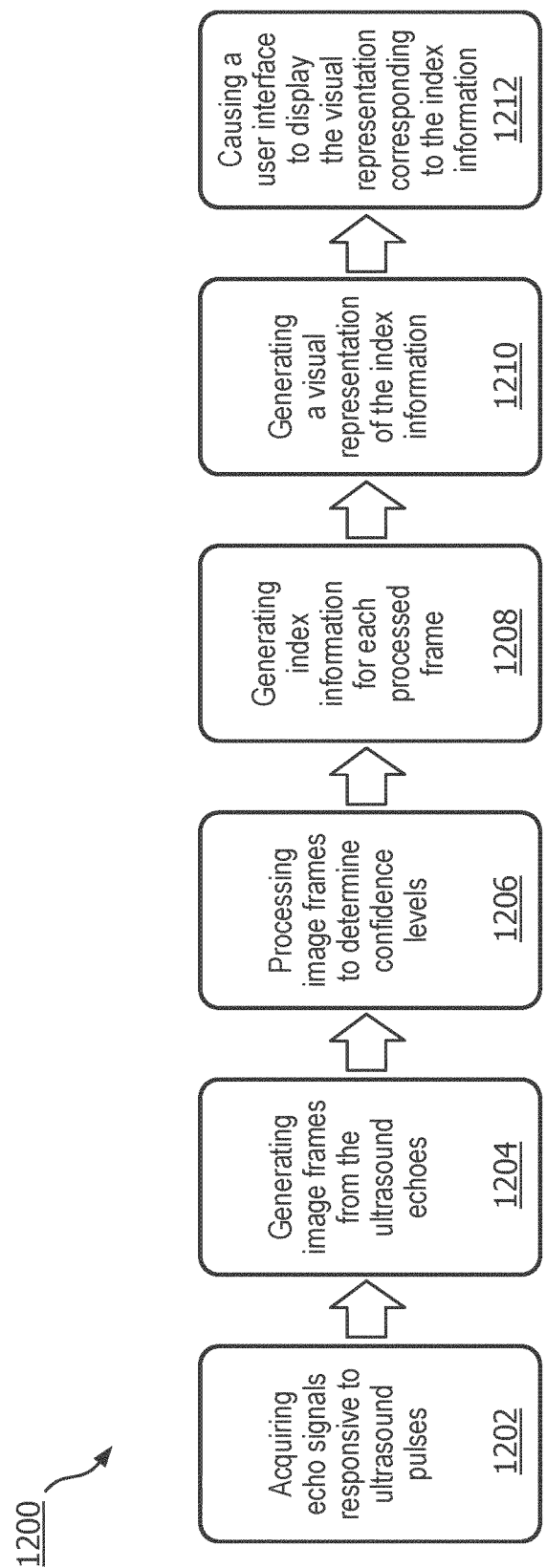
FIG. 12 is a block diagram of a method in accordance with principles of the present disclosure.

FIG. 12 is a flow diagram of a method 1200 of ultrasound imaging performed in accordance with principles of the present disclosure. The example method 1200 shows the steps that may be utilized, in any sequence, by the systems and/or apparatuses described herein for determining items of interest present in an image frame. The method 1200 may be performed by an ultrasound imaging system, such as system 100, or other systems including, but not limited to, for example, a mobile system such as LUMIFY by Koninklijke Philips N.V. ("Philips"). Additional example systems may include, but are not limited to, SPARQ and/or EPIQ, also produced by Philips.

In the embodiment shown, the method 1200 begins at block 1202 by acquiring echo signals responsive to ultrasound pulses transmitted into a region of interest by a transducer operatively coupled to an ultrasound system.

At block 1204, the method involves, generating image frames from the ultrasound echoes.

At block 1206, the method involves, processing each of a plurality of image frames to determine whether a confidence level, wherein the confidence level is a probability that a target anatomical feature is present in the image frames. In some embodiments, the determination may be made for more than one target anatomical feature. Block 1206 may be performed by neural network 128 in some embodiments.

At block 1208, the method involves, generating, for each processed frame, index information based on the confidence level for each frame. Block 1208 may be performed by neural network 128 in some embodiments.

At block 1210, the method involves, generating a visual representation of the index information. In some embodiments, block 1210 may be performed by the display processor 158. In some embodiments, a visual representation of the confidence levels may also be generated.

A block 1212, the method involves, causing a user interface to display the visual representation corresponding to the index information. In some embodiments, block 1212 may be performed by display processor 158. In some embodiments, the visual representation including confidence levels may be displayed.

In some embodiments, method 1200 may further include determining merit levels and/or acquiring a measurement of the target anatomical feature present in an image frame. These additional steps may be performed by image quality network 144 and/or image measurement network 148. In some embodiments, visual representations of the merit levels and/or measurements may be generated and displayed. In some embodiments, this may be performed by display processor 158.

Although the examples described herein refer to a current ultrasound exam or review of a prior exam, principles of the present disclosure can be applied to review of multiple exams. The exams may be of a single subject, for example, when reviewing a patient for the progression of a disease. The exams may be of multiple subjects, for example, when identifying an item of interest across a population for a medical study.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "C#", "Java", "Python", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
an ultrasound transducer configured to acquire echo signals responsive to ultrasound pulses transmitted toward a region of interest;
one or more processors in communication with the ultrasound transducer and configured to:
receive a plurality of image frames generated from the ultrasound echoes;
determine, for each image frame of the plurality of image frames, whether target anatomical feature is present in the image frames; and
generate, for each of the image frames of the plurality of image frames, index information based on a confidence level indicating the target anatomical feature is present in the given image frame; and
a user interface in communication with the one or more processors and configured to display a visual representation of the index information,
wherein the visual representation comprises a marker associated with the target anatomical feature, and wherein the visual representation further includes a first axis representing an order of the plurality of image frames and wherein the maker is located on the first axis at a location representing the given image frame where the target anatomical feature is present.

2. The ultrasound imaging system of claim 1, wherein the visual representation further includes a legend indicating the marker is associated with the target anatomical feature.

3. The ultrasound imaging system of claim 1, wherein the visual representation further includes a second axis representing a magnitude of the confidence level.

4. The ultrasound imaging system of claim 1, wherein the marker includes a visual characteristic that varies based on the confidence level.

5. The ultrasound imaging system of claim 4, wherein the visual characteristic is at least one of color or height.

6. The ultrasound system of claim 1, wherein the user interface includes a selector configured to be controlled by a user input.

7. The ultrasound system of claim 6, wherein the user input determines a location of the selector on the visual representation and the location determines an image frame of the plurality of image frames to be displayed, and optionally wherein the location is on the marker.

8. The ultrasound imaging system of claim 1, wherein the one or more processors are configured to determine whether the target anatomical feature is present in the image frames by inputting the frames into a neural network trained with imaging data comprising the target anatomical feature.

9. The ultrasound imaging system of claim 1, wherein the visual representation is configured to display the index information based on the confidence levels above a threshold value.

10. he ultrasound imaging system of claim 1, wherein the one or more processors are configured to determine that a standard view has been acquired and the user interface is configured to display a list of standard views and a graphical indicator on the list indicating that the standard view has been acquired.

11. The ultrasound imaging system of claim 1, wherein the one or more processors are further configured to determine merit levels based on the index information of the plurality of image frames, the merit levels associated with a quality of the image frames.

12. A method comprising:
acquiring echo signals responsive to ultrasound pulses transmitted into a region of interest by a transducer operatively coupled to an ultrasound system;
generating a plurality of image frames from the ultrasound echoes;
processing each of a plurality of image frames to determine a confidence level, wherein the confidence level is a probability that a target anatomical feature is present in the image frame;
generating, for each processed frame, index information based on the confidence level for each frame;
generating a visual representation of the index information; and
causing a user interface to display the visual representation corresponding to the index information,
wherein the visual representation comprises a first axis representation an order of the plurality of image frames and a plurality of markers located on the first axis at locations representing the image frames where the target anatomical feature is present.

13. The method of claim 12, further comprising generating merit levels of the image frames where the target anatomical feature is present, the merit levels associated with an image quality of the respective image frames, and
optionally wherein the method further comprises displaying an image of the frames having a highest merit level.

14. The method of claim 12, further comprising making a measurement of the target anatomical feature from an image frame where the target anatomical feature is present.

15. The method of claim 12, further comprising causing the user interface to display a selector with the visual representation, wherein the selector may determine an image frame of the plurality of image frames to be displayed by the user interface based on a user input.

* * * * *